United States Patent [19]

Cauwet et al.

[11] Patent Number: 5,656,258
[45] Date of Patent: Aug. 12, 1997

[54] COSMETIC COMPOSITION CONTAINING A MIXTURE OF CONDITIONING POLYMERS

[75] Inventors: Danièle Cauwet, Paris; Claude Dubief, Le Chesnay, both of France

[73] Assignee: L'Oreal, Paris, France

[21] Appl. No.: 357,027

[22] Filed: Dec. 16, 1994

[30] Foreign Application Priority Data

Dec. 27, 1993 [FR] France .................... 93 15691

[51] Int. Cl.⁶ .................... A61K 7/06; A61K 7/48
[52] U.S. Cl. .................... 424/70.17; 424/401; 424/70.11; 424/78.03
[58] Field of Search .................... 424/70.12, 401, 424/70.11, 70.17, 78.03; 252/174.23, DIG. 2, DIG. 5, DIG. 13

[56] References Cited

U.S. PATENT DOCUMENTS

| | | |
|---|---|---|
| 2,528,378 | 10/1950 | Mannheimer et al. |
| 2,781,354 | 2/1957 | Mannheimer et al. |
| 4,217,914 | 8/1980 | Jacquet et al. |
| 4,349,532 | 9/1982 | Vanlerberghe et al. .................... 424/47 |
| 4,422,853 | 12/1983 | Jacquet et al. |
| 4,764,365 | 8/1988 | Boothe et al. .................... 514/772.6 |
| 4,772,462 | 9/1988 | Boothe et al. .................... 424/70.16 |
| 4,948,579 | 8/1990 | Jacquet et al. |
| 4,996,059 | 2/1991 | Grollier et al. |
| 5,089,252 | 2/1992 | Grollier et al. |
| 5,114,428 | 5/1992 | Hoeffkes et al. .................... 8/405 |
| 5,132,107 | 7/1992 | Lange .................... 514/345 |
| 5,139,037 | 8/1992 | Grollier et al. |
| 5,196,189 | 3/1993 | Jacquet et al. |
| 5,275,755 | 1/1994 | Sebag et al. .................... 252/174.15 |
| 5,449,475 | 9/1995 | Cauwet et al. .................... 252/174.23 |

FOREIGN PATENT DOCUMENTS

| | | |
|---|---|---|
| 0269243 | 6/1988 | European Pat. Off. |
| 0557203 | 8/1993 | European Pat. Off. |
| 2270846 | 12/1975 | France . |
| 2470596 | 6/1981 | France . |
| 2519863 | 7/1983 | France . |
| 2063671 | 6/1981 | United Kingdom . |
| 2114580 | 8/1983 | United Kingdom . |

*Primary Examiner*—Melvyn I. Marquis
*Assistant Examiner*—Robert H. Harrison
*Attorney, Agent, or Firm*—Finnegan, Henderson, Farabow, Garrett & Dunner, L.L.P.

[57] ABSTRACT

A cosmetic composition comprising at least one quaternary polyammonium polymer (a) and at least one polymer (b) containing about 70 to 90% by weight of diallyldialkylammonium units in a weight ratio (a)/(b) equal to less than 1. A method of using such a composition for hair and/or skin care. This composition makes it possible to improve the disentanglement of hair (especially wet hair) as well as the softness of the hair and the skin.

28 Claims, No Drawings

COSMETIC COMPOSITION CONTAINING A MIXTURE OF CONDITIONING POLYMERS

The present invention is directed to cosmetic compositions for the hair and the skin containing conditioning polymers.

The use of polymeric, especially cationic, conditioners in order to facilitate the disentangling of hair and to impart softness and suppleness on the hair has already been recommended in compositions for the washing or the care of the hair. The use of cationic polymers for this purpose, however, has various disadvantages. Because of their high affinity for the hair, some of these polymers substantially deposit onto the hair during repeated use, and lead to undesirable effects such as an unpleasant feel, stiffening of the hair, and interfibre adhesion affecting hair-styling. These disadvantages are accentuated in the case of fine hair, which lacks retention, vitality and body.

Among the prior art documents which describe the use of cationic polymers as cosmetic agents there may be mentioned French Patent Application No. FR-A-2,270,846, the disclosure of which is incorporated by reference, and its U.S. counterparts, U.S. Pat. No. 4,217,914, U.S. Pat. No. 4,422,853, U.S. Pat. No. 4,948,579 and U.S. Pat. No. 5,196,189, the disclosures of which are incorporated by reference, which describe the use of quaternized polymers. The use of these quaternized polymers as sole cosmetic treatment agents is not completely satisfactory with regard to hair retention.

The use of amphoteric polymers such as those described in European Patent Application No. EP-A-269 243, the disclosure of which is incorporated by reference, has also been recommended for improving the conditioning properties of hair products. However, compositions containing only these polymers do not make it possible to obtain sufficient softness and disentanglement.

Moreover, in French Patent Application No. FR-A-2,470,596 and U.S. Pat. No. 4,996,059, the disclosures of which are incorporated by reference, as well as French Patent Application No. FR-A-2,519,863, U.S. Pat. No. 5,089,252 and U.S. Pat. No. 5,139,037, the disclosures of which are incorporated by reference, cosmetic compositions for the treatment of hair containing a combination of a cationic polymer and an amphoteric polymer are provided. While these compositions are superior to compositions containing only a cationic polymer or an amphoteric polymer, they are, however, not completely satisfactory with regard to the properties of disentanglement and softness conferred on the hair.

It has been discovered that the combination of certain conditioning polymers, described in the prior art documents which have been mentioned above, when they are used in a given ratio make it possible to overcome these disadvantages due to a synergistic effect that is achieved.

This combination can offer clearly improved cosmetic properties compared with the properties obtained with either of the constituents used alone, as well as compared with combinations of the two constituents used in ratios outside the field of the invention.

It has been discovered in particular that the compositions obtained according to the present invention can offer an improvement in disentanglement (especially on wet hair) as well as an improvement in the softness of the hair. In addition, build up does not occur on the hair after repeated applications. Moreover, the compositions of the present invention, when applied to the skin, particularly in the form of a bubble bath or a shower gel, can offer improvement in the softness of the skin.

The present invention is thus directed to cosmetic compositions comprising:

at least one quaternary polyammonium polymer (a) comprising recurring units of formula:

in which:

A and B, which may be identical or different, represent polyethylene groups containing 2 to 20 carbon atoms which may be linear or branched, saturated or unsaturated and which may contain, intercalated in the principal chain, one or more —$CH_2$—Y—$CH_2$— groups with Y designating O, S, SO, $SO_2$ or —CHOH—;

$X^-$ represents an union derived from an inorganic or organic acid;

m represents a value such that the molecular mass of polymer (a) ranges from 1000 to 100,000, determined by gel permeation chromatography;

$R_1$, $R_2$, $R_3$ and $R_4$, which may be identical or different, represent an alkyl or hydroxyalkyl radical having 1 to 4 carbon atoms; and at least one polymer (b) consisting of about 70 to 90% by weight of diallyldialkylammonium units in which the alkyl radical contains 1 to 18 carbon atoms, and about 30% to 10% by weight of acrylic or methacrylic units, in a weight ratio of the (a) polymer to the (b) copolymer, (a)/(b), equal to less than 1.

A preferred embodiment of the present invention includes: at least one quaternary polyammonium polymer (a) comprising recurring units of formula:

in which:

A and B, which may be identical or different, represent polymethylene groups containing 2 to 20 carbon atoms which may be linear or branched, saturated or unsaturated and which may contain, intercalated in the principal chain, one or more —$CH_2$—Y—$CH_2$— groups with Y designating O, S, SO, $SO_2$ or —CHOH—;

$X^-$ represents an anion derived from an inorganic or organic acid;

m represents a value such that the molecular mass ranges from between 1000 to 100,000;

$R_1$, $R_2$, $R_3$ and $R_4$, which may be identical or different, designate an alkyl or hydroxyalkyl radical having 1 to 4 carbon atoms; and at least one polymer (b) consisting of 70 to 90% by weight of diallyldialkylammonium units in which the alkyl radical contains 1 to 18 carbon atoms, and 30% to 10% by weight of acrylic or methacrylic units, the weight ratio between the (a) polymer and the (b) copolymer being synergistically effective with respect to at least one cosmetic property.

Preferred (a) polymers include those comprising recurring units of formula:

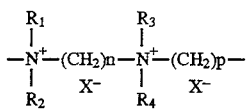
(a)

in which $R_1$, $R_2$, $R_3$ and $R_4$, which may be identical or different, represent an alkyl or hydroxyalkyl radical having about 1 to 4 carbon atoms; n and p represent integers ranging from about 2 to 20; and $X^-$ represents an anion derived from an inorganic or organic acid.

More preferred (a) polymers include the compounds in which $R_1$, $R_2$, $R_3$ and $R_4$ represent a methyl or ethyl radical and $X^-$ represents a halogen atom selected from chlorine, iodine or bromine. A particularly preferred compound of formula (a) is that in which $R_1$, $R_2$, $R_3$ and $R_4$ represent a methyl radical; n=3; p=6; and X=Cl. Another particularly preferred compound of formula (a) is that in which $R_1$ and $R_2$ represent a methyl radical; $R_3$ and $R_4$ represent an ethyl radical; n=p=3; and X=Br.

Among the (b) polymers, there are preferred the copolymers of diallyldimethylammonium or diallyldiethylammonium chloride and acrylic acid with a molecular weight, determined by gel permeation chromatography, ranging from 50,000 to 10,000,000 and preferably from 200,000 to 5,000,000. A particularly preferred polymer of this type is the copolymer of diallyldimethylammonium chloride and acrylic acid (80/20 by weight) sold as a solution containing 35% active material by the company CALGON CORP under the name MERQUAT 280.

Preferably, the ratio (a)/(b) is less than or equal to 0.75. Still more preferably, the ratio (a)/(b) is less than or equal to 0.5.

In the compositions according to the invention, the proportion by weight of the (a) polymer preferably ranges from 0.05% to 4%, and still more preferably ranges from 0.1% to 3%; that of the (b) polymer preferably ranges from 0.1% to 8% and still more preferably ranges from 0.2% to 6%, relative to the total weight of the composition.

The compositions of the invention preferably additionally contain at least one surfactant in a quantity ranging from about 0.1% to 40% by weight, preferably from 3% to 40% and still more preferably from 5% and 30%, relative to the total weight of the composition. This surfactant may be chosen from an anionic, amphoteric, zwitterionic, non-ionic or cationic surfactant or mixtures thereof.

Among the anionic surfactants, there may be mentioned the salts (in particular alkali metal salts, especially of sodium, ammonium salts, amine salts, amino alcohol salts or magnesium salts) of the following compounds: alkyl ether sulphates, alkyl amidoether sulphates, alkyl aryl polyether sulphates, monoglyceride sulphates; alkyl sulphonates, alkyl sulphates, alkyl phosphates, alkyl amide sulphonates, alkyl aryl sulphonates, α-olefin sulphonates, paraffin sulphonates; alkyl sulphosuccinates, alkyl ether sulphosuccinates, alkyl amide sulphosuccinates; alkyl sulphosuccinamates; alkyl sulphoacetates; alkyl ether phosphates; acyl sarcosinates and N-acyltaurates. The alkyl or acyl radical of these various compounds preferably contains 12 to 20 carbon atoms.

Among the anionic surfactants, there may be mentioned fatty acid salts such as the salts of oleic, ricinoleic, palmitic and stearic acid, copra oil or hydrogenated copra oil acids; acyl lactylates whose acyl radical contains 8 to 20 carbon atoms. It is also possible to use weakly anionic surfactants such as alkyl-D-galactoside-uronic acids and their salts as well as polyoxyalkylenated ether carboxylic acids, in particular those containing 2 to 24 ethylene oxide groups, and mixtures thereof. The anionic surfactants of the polyoxy-alkylenated ether carboxylic acid type are in preferably those which correspond to the formula (i):

$$R_5-(OC_3H_6)q-(OC_2H_4)r-OCH_2COOA \quad (i)$$

in which:

$R_5$ designates a linear or branched $C_8$–$C_{22}$ alkyl or alkenyl group, a ($C_8$–$C_9$ alkyl)phenyl, a group $R'$—CONH—$CH_2$— with R' designating a $C_{11}$–$C_{21}$ alkyl or alkenyl, q is an integer or a decimal which may range from 0 to 6, and r is an integer or decimal which may range from 2 to 24, and preferably from 3 to 10. A designates H, ammonium, Na, K, Li, Mg or a monoethanolamine or triethanolamine residue. It is also possible to use mixtures of compounds of formula (i), in particular mixtures in which the $R_5$ groups are different. Compounds of formula (i) are sold for example by the company CHEM Y under the names AKYPOS (NP40, NP70, OP40, OP80, RLM25, RLM38, RLMQ 38 NV, RLM 45, RLM 45 NV, RLM 100, RLM 100 NV, RO 20, RO 90, RCS 60, RS 60, RS 100, RO 50) or the company SANDOZ under the name SANDOPAN (DTC Acid, DTC).

According to a preferred embodiment of the invention, there is used as anionic surfactant at least one compound of the carboxylic acid type which is of the formula (i) indicated above, in which $R_5$ designates a ($C_{12}$–$C_{14}$)alkyl, oleyl, cetyl or stearyl radical, A designates a hydrogen or sodium atom, q=0 and r ranges from 3 to 10. The product marketed by the company CHEM Y under the name RLM 45 is for example used ($R_5$: ($C_{12}$–$C_{14}$)alkyl, mean value of r=4.5, q=0 and A=H).

The non-ionic surfactants may be chosen from alcohols, alpha-diols, alkylphenols or polyethoxylated, polypropoxylated and polyglycerolated fatty acids, having a fatty chain containing for example 8 to 18 carbon atoms, it being possible for the number of ethylene oxide or propylene oxide groups to preferably range from 2 to 50 and it being possible for the number of glycerol groups to preferably range from 2 to 30. It is also possible to mention ethylene and propylene oxide copolymers, condensates of ethylene and propylene oxide with fatty alcohols; polyethoxylated fatty amides preferably having 2 to 30 moles of ethylene oxide, polyglycerolated fatty amides containing on average 1 to 5 glycerol groups and in particular 1.5 to 4; polyethoxylated fatty amines having preferably 2 to 30 moles of ethylene oxide; oxyethylenated sorbitan fatty acid esters having 2 to 30 moles of ethylene oxide; sucrose fatty acid esters, polyethylene glycol fatty acid esters, alkyl polyglycosides, N-alkylglucamine derivatives, amine oxides such as ($C_{10}$–$C_{14}$ alkyl)amine oxides or N-acylaminopropylmorpholine oxides. The alkylpolyglycosides and the polyglycerolated compounds are part of the more particularly preferred non-ionic surfactants.

The preferred amphoteric or zwitterionic surfactants are derivatives of aliphatic secondary or tertiary amines in which the aliphatic radical is a linear or branched chain containing 8 to 18 carbon atoms and containing at least one water-solubilizing anionic group (for example carboxylate, sulphonate, sulphate, phosphate or phosphonate); there may also be mentioned ($C_8$–$C_{20}$)alkyl betaines, sulphobetaines, ($C_8$–$C_{20}$)alkyl amido($C_1$–$C_6$ alkyl) betaines or ($C_8$–$C_{20}$) alkyl amido($C_1$–$C_6$ alkyl) sulphobetaines.

Among the amine derivatives, there may be mentioned the products sold under the name MIRANOL, as described in U.S. Pat. No. 2,528,378 and U.S. Pat. No. 2,781,354, the disclosures of which are incorporated by reference, and classified in the Cosmetic, Toiletry and Fragrance Association dictionary, 3rd edition (1982), under the names Amphocarboxylglycinates and Amphocarboxypropionates with the respective structures:

$R_6$—CONHCH$_2$CH$_2$—N(R$_7$)(R$_8$)(CH$_2$COO$^-$)

in which:

$R_6$ designates an alkyl radical of an acid $R_6$—COOH which is present in hydrolysed copra oil, a heptyl, nonyl or undecyl radical; $R_7$ designates a beta-hydroxyethyl group; and $R_8$ designates a carboxymethyl group; and $R_9$—CONHCH$_2$CH$_2$—N(B)(C)

in which:

B represents —CH$_2$CH$_2$OX'; C represents —(CH$_2$)$_z$—Y', z=1 or 2; X' designates the group —CH$_2$CH$_2$—COOH or a hydrogen atom; Y' designates —COOH or the radical —CH$_2$—CHOH—SO$_3$H; and $R_9$ designates an alkyl radical of an acid $R_9$—COOH which is present in copra oil or in hydrolysed linseed oil, an alkyl radical, especially a $C_7$, $C_9$, $C_{11}$ or $C_{13}$, a $C_{17}$ alkyl radical and its iso form, or an unsaturated $C_{17}$ radical. As an example, there may be mentioned cocoamphocarboxyglycinate sold under the trade name MIRANOL C$_2$M Conc. by the company RHONE POULENC.

Among the cationic surfactants, there may be mentioned in particular: the salts of optionally polyoxyalkylenated primary, secondary or tertiary fatty amines; quaternary ammonium salts such as tetraalkylammonium, alkylamidoalkyltrialkyammonium, trialkylbenzylammonium, trialkylhydroxyalkylammonium or alkylpyridinium chlorides or bromides; imidazoline derivatives; or amine oxides of cationic character. The concentration of these cationic surfactants preferably ranges from 0.1% to 10% by weight relative to the total weight of the composition.

The anionic surfactants are preferably used in the form of a mixture with amphoteric surfactants. In this case, the weight ratio of the first to the second can range from 0.5 to 10, and preferably from 1 to 5.

The compositions in accordance with the invention may contain, in addition, customary adjuvants. Typical adjuvants include perfumes, solvents, preservatives, sequestrants, thickeners, emollients, foam modifiers, acidifiers and alkalizing agents.

The thickening agents may be chosen preferably from sodium alginate, gum arabic, cellulose derivatives such as methylcellulose, hydroxymethylcellulose, hydroxyethyl cellulose, hydroxypropyl cellulose, hydroxypropyl methylcellulose, guar gum or its derivatives, xanthan gums, scleroglucans, cross-linked polyacrylic acids, oxyethylenated propylene glycol oleate containing 55 moles of ethylene oxide and esters of fatty alcohols having 27 to 44 carbon atoms. The thickener can also be obtained by mixing the polyethylene glycol with polyethylene glycol stearates or distearates, or by mixing phosphoric esters and amides. These thickeners are preferably used in proportions ranging from 0.5% to 5% by weight relative to the total weight of the composition.

The aqueous medium for the polymers and active ingredients may contain, in addition to water, cosmetically acceptable solvents such as monoalcohols, polyalcohols, glycol ethers or fatty acid esters, used alone or as a mixture. Among these solvents, there may be mentioned more particularly lower alcohols such as ethanol, isopropanol; polyalcohols such as ethylene glycol, diethylene glycol, propylene glycol, glycol ethers and glycol or diethylene glycol alkyl ethers. The solvents are preferably used in proportions ranging from 0.5% to 10% by weight relative to the total weight of the composition.

The compositions according to the invention may also contain dyes, viscosity-modifying agents, pearlescent agents, moisturizing agents, anti-dandruff agents, anti-seborrhoeic agents, sunscreens, volatile or non-volatile silicones, organomodified or otherwise, other conditioning agents, apart from those of the invention such as polymeric or non-polymeric cationic compounds, hydrocarbon oils, proteins, vitamins and the like.

The pH of the compositions according to the invention generally ranges from 4 to 8 and preferably from 5 to 7.

The compositions in accordance with the invention can be used for washing and treating the hair and/or the skin.

The compositions of the invention may be more particularly in the form of an after-shampoo to be rinsed off or otherwise, compositions for permanent waving, hair straightening, dyeing or bleaching, or alternatively in the form of rinse-off compositions to be applied before or after dyeing, bleaching, permanent waving or hair straightening or alternatively between the two stages of a permanent waving or hair straightening process. The compositions of the invention may also be in the form of washing compositions for the body, and in particular in the form of bath or shower solutions or gels or make-up removing products. The compositions according to the invention may also be in the form of aqueous or aqueous-alcoholic lotions for skin or hair care.

A person skilled in the art will determine, among the various additives listed above, those which are suitable for the desired application.

The following examples illustrate the invention without limiting the scope of the invention.

EXAMPLE 1

A disentangling lotion for use after permanent waving was prepared containing:

a) a polymer (a) consisting of recurring units having the structure

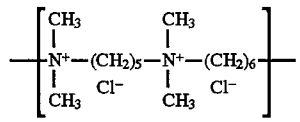

whose molecular weight, determined by gel permeation chromatography, ranged from 9500 to 9900; x g b) a diallyldimethylammonium chloride/acrylic acid copolymer which contained 35% active ingredient (AI) sold under the name MERQUAT 280 by the company CALGON; y g

| | |
|---|---|
| HCl qs | pH 5.5 |
| Preservatives qs | |
| Water qs | 100 g |

Five lotions of this type: I, II, III, IV, V, having 5 different (a)/(b) polymer ratios, respectively: 1.5/1/0.75/0.5/0.1 were each compared with lotions A and B, i.e., IA and IB for lotion I, IIA and IIB for lotion II, IIIA and IIIB for lotion III, IVA and IVB for lotion IV, VA and VB for lotion V. The A lotions contained only the (a) polymer at the concentration x+y, the B lotions contained only the (b) polymer at the concentration x+y.

The polymer composition of these lotions is expressed in the table below:

| POLYMERS | I | IA | IB | II | IIA | IIB | III | IIIA | IIIB | IV | IVA | IVB | V | VA | VB |
|---|---|---|---|---|---|---|---|---|---|---|---|---|---|---|---|
| (x) in g | 1.05 | 1.75 | — | 1 | 2 | — | 0.75 | 1.75 | — | 0.5 | 1.5 | — | 0.1 | 1.1 | — |
| (y) in g | 0.7 | — | 1.75 | 1 | — | 2 | 1 | — | 3.75 | 1 | — | 1.5 | 1 | — | 1.1 |
| Ratio (a)/(b) | 1.5 | — | — | 1 | — | — | 0.75 | — | — | 0.5 | — | — | 0.1 | — | — |

2.5 g of locks of permanently-waved hair were treated respectively with the 15 compositions shown in the above table, and then rinsed with water after allowing to act for 2 minutes.

The disentanglement, in the wet state, of the hair treated with these lotions was then compared by means of a sensory evaluation test.

The object of the test used was the specification, by a panel of judges, of each series of 3 samples as an increasing or decreasing function of the efficacy of the disentanglement. The 3 locks from the same series were presented simultaneously to the panel. The panel was asked to classify them from the easiest to disentangle to the most difficult. Statistical analysis of the results was performed by means of the A. KRAMER tables (Food Technology 17-(12), 124–125 1963).

| LOTIONS | \multicolumn{10}{c}{JUDGES} | |
|---|---|---|---|---|---|---|---|---|---|---|---|

| LOTIONS | 1 | 2 | 3 | 4 | 5 | 6 | 7 | 8 | 9 | 10 | RANK SUM |
|---|---|---|---|---|---|---|---|---|---|---|---|
| I | 2 | 2 | 2 | 2 | 2 | 2 | 2 | 2 | 2 | 2 | 20 |
| IA | 3 | 3 | 3 | 3 | 3 | 3 | 3 | 3 | 3 | 3 | 30 |
| IB | 1 | 1 | 1 | 1 | 1 | 1 | 1 | 1 | 1 | 1 | 10 |
| II | 2 | 2 | 2 | 2 | 1 | 2 | 2 | 2 | 2 | 2 | 19 |
| IIA | 3 | 3 | 3 | 3 | 3 | 3 | 3 | 3 | 3 | 3 | 30 |
| IIB | 1 | 1 | 1 | 1 | 2 | 1 | 1 | 1 | 1 | 1 | 11 |
| III | 1 | 1 | 1 | 1 | 1 | 1 | 1 | 1 | 1 | 1 | 10 |
| IIIA | 3 | 3 | 3 | 3 | 3 | 3 | 3 | 3 | 3 | 3 | 30 |
| IIIB | 2 | 2 | 2 | 2 | 2 | 2 | 2 | 2 | 2 | 2 | 20 |
| IV | 1 | 1 | 1 | 2 | 1 | 1 | 1 | 1 | 1 | 1 | 11 |
| IVA | 2 | 2 | 2 | 1 | 2 | 2 | 2 | 2 | 2 | 2 | 19 |
| IVB | 3 | 3 | 3 | 3 | 3 | 3 | 3 | 3 | 3 | 3 | 30 |
| V | 1 | 1 | 1 | 1 | 1 | 2 | 1 | 1 | 1 | 1 | 11 |
| VA | 2 | 2 | 2 | 2 | 2 | 1 | 2 | 2 | 2 | 2 | 19 |
| VB | 3 | 3 | 3 | 3 | 3 | 3 | 3 | 3 | 3 | 3 | 30 |

CONCLUSION

For lotions III, IV, and V according to the invention, the results obtained with the locks treated with the lotions containing the mixture of the (a) and (b) polymers were significantly superior to those obtained with the other two lotions wherein only one of the polymers (a) or (b) was present, at the 5% threshold, i.e., a 5% risk of having a non-synergistic effect.

Lotions III, IV and V for which the (a)/(b) was respectively 0.75; 0.5; 0.1 represent a synergistic effect compared to lotions I and II with (a)/(b) polymer ratios of 1.5 and 1.

EXAMPLE 2

Lotion IV of Example 1, which contained 0.5 g of (a) polymer and 1 g of (b) polymer, was compared with a lotion IV C which contained only 0.5 g of (a) polymer.

2.5 g of permanently-waved hair locks were treated with lotions IV and IVC respectively, rinsed with water after allowing to act for 5 minutes, then dried under a hood dryer.

A second application of the lotions, rinsing and drying was performed, and using the sensory evaluation described in Example 1, the panel was asked to classify the locks as a function of the build up (load effect by the polymer).

RESULTS

| LOTIONS | \multicolumn{10}{c}{JUDGES} | |
|---|---|---|---|---|---|---|---|---|---|---|---|

| LOTIONS | 1 | 2 | 3 | 4 | 5 | 6 | 7 | 8 | 9 | 10 | RANK SUM |
|---|---|---|---|---|---|---|---|---|---|---|---|
| IV | 1 | 1 | 1 | 1 | 1 | 1 | 1 | 1 | 1 | 1 | 10 |
| IVC | 2 | 2 | 2 | 2 | 2 | 2 | 2 | 2 | 2 | 2 | 20 |

Strictly identical results were obtained when a shampoo was performed between the two applications of lotion.

CONCLUSION

Lotion IV according to the invention did not make the hair heavy during repeated applications contrary to lotion IVC which contained only the (a) polymer at 0.5%.

Identical results were obtained with a lotion IVD which contained only the (a) polymer at 1.5%.

EXAMPLE 3

A shampoo having the following composition was prepared:

| | |
|---|---|
| ($C_9$–$C_{10}$–$C_{11}$/20–40—40)alkyl polyglycoside sold at 50% AI by the company HENKEL under the name APG 300 | 15 g AI |
| Polymer of formula (a) consisting of recurring units having the structure: | 0.2 g |

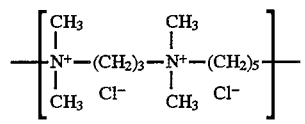

| | |
|---|---|
| whose molecular weight, determined by gel permeation chromatography, was between 9500 and 9900 | |
| Diallyldimethylammonium chloride/acrylic acid copolymer sold under the name MERQUAT 280 by the company CALGON at 35% AI | 1 g AI |
| Hydrochloric acid qs | pH 5 |
| Preservatives, perfume, dye | qs |
| Water qs | 100 g |

EXAMPLE 4

A shampoo having the following composition was prepared:

| | |
|---|---|
| (C12–C14/70-30)alkyl ether carboxylic acid oxyethylenated with 4.5 moles of ethylene oxide (EO), sold as 90% active ingredient solution (AI) under the name AKYPO RLM 45 by the company CHEM'Y | 12 g AI |
| Cocoamphocarboxyglycinate (CTFA, 3rd edition, 1982) sold under the name MIRANOL C2M Conc. by the company RHONE POULENC in aqueous solution at 38% active ingredient (AI) | 8 g AI |
| Polymer of formula (a) as described in Example 3 | 0.75 g |
| Diallyldimethylammonium chloride/acrylic acid copolymer sold under the name MERQUAT 280 by the company CALGON at 35% AI | 1 g AI |
| Oxyethylenated propylene glycol oleate with 55 moles of ethylene oxide and esterified with oleic acid, sold in solution at 43.6% active ingredient under the name ANTIL 141 LIQUID by the company GOLDSCHMIDT | 1.2 g AI |
| NaOH qs | pH 7 |
| Preservatives, perfume, qs | |
| Water qs | 100 g |

EXAMPLE 5

A shampoo having the following composition was prepared:

| | |
|---|---|
| Triethanolamine lauryl sulphate in solution at 40% AI | 16 g AI |
| Copra acid monoisopropanolamide | 2 g |
| Polymer of formula (a) as described in Example 3 | 0.5 g |
| Fatty alcohol ether of formula $C_{16}H_{33}$—O[$C_2H_3$(OH)]($CH_2$)$_2$—$C_{14}H_{29}$ | 2.5 g |
| Diallyldimethylammonium chloride/acrylic acid copolymer sold under the name MERQUAT 280 by the company CALGON at 35% AI | 1.6 g AI |
| Preservatives, perfume qs | |
| Hydrochloric acid qs | pH 4 |
| Water qs | 100 g |

EXAMPLE 6

A conditioner to be rinsed off/rinse having the following composition was prepared:

| | |
|---|---|
| Polymer of formula (a) as described in Example 3 | 0.75 g |
| Diallyldimethylammonium chloride/acrylic acid copolymer sold under the name MERQUAT 280 by the company CALGON at 35% AI | 1 g MA |
| Behenyltrimethylammonium chloride sold under the trade name "GENAMIN KDM-F" by the company HOECHST | 2 g |
| Mixture (80/20) of cetyl steryl alcohol and oxyethylenated cetyl stearyl alcohol at 33 moles of ethylene oxide sold under the name SINNOWAX AO by the company HENKEL | 3 g |
| Hydrochloric acid qs | pH 4 |
| Water qs | 100 g |

EXAMPLE 7

An after-shampoo having the following composition was prepared:

| | |
|---|---|
| Trimethylcetylammonium chloride sold in solution at 25% AI by the company HENKEL under the name DEHYQUART A | 3 g AI |
| Polymer of formula (a) as described in Example 3 | 1 g |
| Diallyldimethylammonium chloride/acrylic acid copolymer sold under the name MERQUAT 280 by the company CALGON at 35% AI | 2.5 g AI |
| Hydroxypropylated guar gum sold by the company MEYHALL under the name JAGUAR HP8 | 1 g |
| Polyethyleneglycol (150 EO) sold by the company UNION CARBIDE under the name CARBOWAX 8000 | 2.5 g |
| Hydrochloric acid qs | pH 4 |
| Preservative, perfume, qs | |
| Water qs | 100 g |

EXAMPLE 8

A shower gel having the following composition was prepared:

| | |
|---|---|
| Polyoxyethylenated (C12–C14/70-30)alkyl ether carboxylic acid at 4.5 moles of EO, sold at 90% active ingredient (AI) under the name AKYPO RLM 45 by the company CHEM'Y | 15 g AI |
| Oxyethylenated sodium lauryl ether sulphate at 2.2 moles of EO, sold in solution at 28% AI | 10 g AI |
| Polymer of formula (a) as described in Example 3 | 0.05 g |
| Diallyldimethylammonium chloride/acrylic acid copolymer sold under the name MERQUAT 280 by the company CALGON at 35% AI | 0.1 g AI |
| Glycerin | 2 g |
| NaOH qs | pH 7 |
| Preservatives, perfume, qs | |
| Water qs | 100 g |

EXAMPLE 9

A shower gel having the following composition was prepared:

| | |
|---|---|
| Oxyethylenated sodium ($C_{12}$–$C_{14}$/70-30)lauryl ether sulphate at 2.2 moles of ethylene oxide sold at 28% active ingredient (AI) | 20 g AI |
| Cocoamidopropylbetaine sold at 30% AI by the company GOLDSCHMIDT under the name TEGOBETAIN HS | 5 g AI |
| Polymer of formula (a) consisting of recurring units of structure: | 0.5 g AI |

$$-\left[\begin{array}{cc} CH_3 & C_2H_3 \\ | & | \\ N^+ - (CH_2)_3 - N^+ - (CH_2)_3 \\ | & | \\ CH_3 \quad Br^- & C_2H_3 \quad Br^- \end{array}\right]-$$

whose molecular weight, determined by gel permeation chromatography was about 1200

| | |
|---|---|
| Diallyldimethylammonium chloride/acrylic acid copolymer sold under the name MERQUAT 280 by the company CALGON at 35% AI | 1 g AI |
| NaOH qs | pH 7 |
| Preservative: qs | |
| Water qs | 100 g |

What is claimed is:

1. A cosmetic composition comprising:

at least one quaternary polyammonium polymer (a) comprising recurring units of formula:

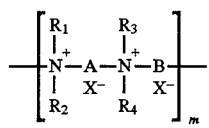

in which:

A and B, which may be identical or different, represent polyethylene groups containing 2 to 20 carbon atoms which may be linear or branched, saturated or unsaturated;

$X^-$ represents an action derived from an inorganic or organic acid;

m represents a value such that polymer (a) in combination with polymer (b) is synergistically effective with respect to at least one cosmetic property;

$R_1$, $R_2$, $R_3$ and $R_4$, which may be identical or different, represent an alkyl or hydroxyalkyl radical having 1 to 4 carbon atoms; and at least one polymer (b) consisting of about 70 to 90% by weight of diallyldialkylammonium units in which the alkyl radical contains 1 to 18 carbon atoms, and 30% to 10% by weight of acrylic or methacrylic units, wherein the (a) polymer and the (b) copolymer are present in a weight ratio synergistically effective with respect to at least one cosmetic property.

2. A composition according to claim 1, wherein the (a) polymer comprises recurring units of the formula:

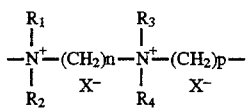

in which $R_1$, $R_2$, $R_3$ and $R_4$, which may be identical or different, represent an alkyl radical having 1 to 4 carbon atoms; n and p are integers ranging from 2 to 20; and $X^-$ represents an anion derived from an inorganic or organic acid.

3. A composition according to claim 1, wherein $R_1$, $R_2$, $R_3$ and $R_4$ represent a methyl or ethyl radical.

4. A composition according to claim 1, wherein $X^-$ is a chlorine atom, an iodine atom or a bromine atom.

5. A composition according to claim 2, wherein the (a) polymer is such that $R_1$, $R_2$, $R_3$ and $R_4$ represent a methyl radical; n=3; p=6; and $X^-$ represents a chlorine atom.

6. A composition according to claim 2, wherein the (a) polymer is such that $R_1$ and $R_2$ represent a methyl radical; $R_3$ and $R_4$ represent an ethyl radical; n=p=3; and X represents a bromine atom.

7. A composition according to claim 1, wherein the molecular weight of the (b) copolymer, determined by gel permeation chromatography, ranges from 50,000 to 10,000,000.

8. A composition according to claim 7, wherein the molecular weight of the (b) copolymer, determined by gel permeation chromatography, ranges 200,000 to 5,000,000.

9. A composition according to claim 1, wherein the (b) copolymer is a copolymer of diallyldimethylammonium or diallydiethylammonium chloride and acrylic acid.

10. A composition according to claim 9, wherein the (b) copolymer has a molecular weight ranging from 200,000 to 5,000,000.

11. A composition according claim 1, wherein the weight ratio between the (a) polymer and the (b) copolymer, a/b, is less than or equal to 0.75.

12. A composition according to claim 11, wherein the molecular ratio between the (a) polymer and the (b) copolymer, a/b, is less than or equal to 0.5.

13. A composition according to claim 1, which comprises the (a) polymer in proportions ranging from 0.05% to 4% by weight relative to the total weight of the composition.

14. A composition according to claim 13, which comprises the (a) polymer in proportions ranging from 0.1% and 3% by weight relative to the total weight of the composition.

15. A composition according to claim 1, which comprises the (b) copolymer in proportions ranging from 0.1% to 8% by weight relative to the total weight of the composition.

16. A composition according to claim 15, which comprises the (b) copolymer in proportions ranging from 0.2% to 6% by weight relative to the total weight of the composition.

17. A composition according to claim 1 which has a pH ranging from 4 to 8.

18. A composition according to claim 17 which has a pH ranging from 5 to 7.

19. A composition according to claim 1, which comprises at least one anionic, cationic, non-ionic, amphoteric or zwitterionic surfactant or mixtures thereof.

20. A composition according to claim 19, in which said at least one surfactant is present in a concentration ranging from 0.1% to 40% by weight relative to the total weight of the composition.

21. A composition according to claim 20, in which said at least one surfactant is present in a concentration ranging from 3% to 40% by weight relative to the total weight of the composition.

22. A composition according to claim 21, in which said at least one surfactant is present in a concentration ranging from 5% to 30% by weight relative to the total weight of the composition.

23. A composition according to claim 1, which comprises at least one additive selected from perfumes, solvents, preservatives, sequestrants, thickeners, emollients, foam-modifying agents, acidifying or alkalinizing agents, dyes, viscosity-modifying agents, pearlescent agents, moisturizing agents, anti-dandruff agents, anti-seborrhoeic agents, sunscreens, volatile or non-volatile silicones and conditioning agents.

24. A formulation comprising the composition of claim 1, wherein said formulation is a shampoo, a conditioner to be rinsed off, a composition for permanent waving or straightening of the hair, a composition for dyeing or bleaching of the hair, a rinse-off composition to be applied between the two stages of a permanent waving or hair straightening process, a washing composition for the body, or a lotion.

25. A method for treating hair and/or skin, comprising contacting the hair or the skin with an amount of the composition according to claim 1 effective to treat the hair or the skin.

26. A cosmetic composition comprising:

at least one quaternary polyammonium polymer (a) comprising recurring units of formula:

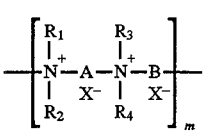

in which:

A and B, which may be identical or different, represent polymethylene groups containing 2 to 20 carbon atoms which may be linear or branched, saturated or unsaturated;

$X^-$ represents an anion derived from an inorganic or organic acid;

m represents a value such that polymer (a) in combination with polymer (b) is synergistically effective with respect to at least one cosmetic property;

$R_1$, $R_2$, $R_3$ and $R_4$, which may be identical or different, represent an alkyl or hydroxyalkyl radical having 1 to 4 carbon atoms; and at least one polymer (b) consisting of about 70 to 90% by weight of diallyldialkylammonium units in which the alkyl radical contains 1 to 18 carbon atoms, and 30% to 10% by weight of acrylic or methacrylic units, in a weight ratio of the (a) polymer to the (b) copolymer equal to less than 1.

27. A composition according to claim 1, wherein the cosmetic property is reduced tangling and/or increased softness of hair.

28. A cosmetic composition comprising:

at least one quaternary polyammonium polymer (a) comprising recurring units of formula:

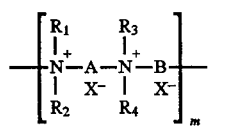
(a)

in which:

A and B, which may be identical or different, represent polymethylene groups containing 2 to 20 carbon atoms which may be linear or branched, saturated or unsaturated;

—$X^-$ represents an anion derived from an inorganic or organic acid;

m represents a value such that polymer (a) in combination with polymer (b) is synergistically effective with respect to at least one cosmetic property;

$R_1$, $R_2$, $R_3$ and $R_4$, which may be identical or different, represent an alkyl or hydroxyalkyl radical having 1 to 4 carbon atoms; and —at least one polymer (b) consisting essentially of about 70 to 90% by weight of diallyldialkylammonium units in which the alkyl radical contains from 1 to 18 carbon atoms, and acrylic or methacrylic units, —wherein the (a) polymer and the (b) polymer are present in a weight ratio synergistically effective with respect to disentangling activity.

* * * * *

UNITED STATES PATENT AND TRADEMARK OFFICE
CERTIFICATE OF CORRECTION

PATENT NO. : 5,656,258
DATED : August 12, 1997
INVENTOR(S) : Danièle CAUWET et al.

It is certified that error appears in the above-indentified patent and that said Letters Patent is hereby corrected as shown below:

In the Claims, claim 1, column 11, line 9, "polyethylene" should read --polymethylene-- line 12, "action" should read --anion--.

Signed and Sealed this

Fourteenth Day of October, 1997

Attest:

BRUCE LEHMAN

*Attesting Officer*    *Commissioner of Patents and Trademarks*